US008862232B2

(12) United States Patent
Zarinetchi et al.

(10) Patent No.: US 8,862,232 B2
(45) Date of Patent: Oct. 14, 2014

(54) TRANSCUTANEOUS ENERGY TRANSFER MODULE WITH INTEGRATED CONVERSION CIRCUITRY

(71) Applicant: Abiomed, Inc., Danvers, MA (US)

(72) Inventors: Farhad Zarinetchi, Chelmsford, MA (US); Anthony Bailey, Beverly, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 13/941,763

(22) Filed: Jul. 15, 2013

(65) Prior Publication Data

US 2013/0304158 A1 Nov. 14, 2013

Related U.S. Application Data

(60) Division of application No. 10/316,138, filed on Dec. 10, 2002, now Pat. No. 8,489,200, which is a continuation-in-part of application No. 09/957,330, filed on Sep. 20, 2001, now Pat. No. 6,496,733, which is a division of application No. 09/346,833, filed on Jul. 2, 1999, now Pat. No. 6,324,431, which is a continuation-in-part of application No. 09/110,607, filed on Jul. 6, 1998, now abandoned.

(51) Int. Cl.
*A61N 1/378* (2006.01)
(52) U.S. Cl.
CPC .............. *A61N 1/378* (2013.01); *A61N 1/3787* (2013.01)
USPC ........................................................... 607/33
(58) Field of Classification Search
USPC .................... 607/32, 33, 36, 60, 61
See application file for complete search history.

(56) References Cited

U.S. PATENT DOCUMENTS 3,195,540 A 7/1965 Waller
3,357,434 A 12/1967 Abell
(Continued)

FOREIGN PATENT DOCUMENTS

DE 2720011 C2 8/1985
EP 0507360 A3 7/1992
(Continued)

OTHER PUBLICATIONS

Abe, Yuusuke, et al., "Development of Transcutaneous Energy Transmission System for Totally Implantable Artificial Heart", Artificial Heart 2/Proceedings of the 2nd International Symposium on Artificial Heart and Assist Device (T. Akutsu, ed.), Tokyo: Springer-Verlag, pp. 257-261 (1988).

(Continued)

*Primary Examiner* — George Evanisko
(74) *Attorney, Agent, or Firm* — Thomas J. Engellenner; Reza Mollaaghababa; Pepper Hamilton LLP

(57) ABSTRACT

An implantable transcutaneous energy transfer device secondary coil module includes a housing, a secondary coil, power conditioning circuitry, and a low voltage, high power connector. The transcutaneous energy transfer secondary coil is disposed outside the housing and is configured to receive a time-varying magnetic field provided by a transcutaneous energy transfer primary coil, and to convert the time-varying magnetic field into a high voltage, alternating current electric signal within the coil. The power conditioning circuitry is mounted within the housing and is electrically coupled to the secondary coil. The power conditioning circuitry including electronics for converting the high voltage, alternating current electric signal from the secondary coil into a high power, low voltage direct current electric signal. The low voltage, high power connector electrically coupled to the power conditioning circuitry and extending outside the housing for connecting the secondary coil module to a power bus for delivering power to implanted devices.

16 Claims, 7 Drawing Sheets

(56) References Cited

U.S. PATENT DOCUMENTS

| | | | |
|---|---|---|---|
| 3,824,129 A | 7/1974 | Fagan et al. | |
| 3,888,260 A | 6/1975 | Fischell | |
| 3,934,177 A | 1/1976 | Horbach | |
| 3,942,535 A | 3/1976 | Schulman | |
| 4,012,769 A | 3/1977 | Edwards et al. | |
| 4,041,955 A | 8/1977 | Kelly et al. | |
| 4,068,292 A | 1/1978 | Berry et al. | |
| 4,071,032 A | 1/1978 | Schulman | |
| 4,104,701 A | 8/1978 | Baranowski | |
| 4,143,661 A | 3/1979 | LaForge et al. | |
| 4,186,749 A | 2/1980 | Fryer | |
| 4,441,498 A | 4/1984 | Nordling | |
| 4,517,585 A | 5/1985 | Ridout et al. | |
| 4,539,433 A | 9/1985 | Ishino et al. | |
| 4,586,508 A | 5/1986 | Batina et al. | |
| 4,665,896 A | 5/1987 | LeForge et al. | |
| 4,679,560 A | 7/1987 | Galbrith | |
| 4,741,339 A | 5/1988 | Harrison et al. | |
| 4,944,299 A | 7/1990 | Silvian | |
| 5,000,178 A | 3/1991 | Griffith | |
| 5,214,392 A | 5/1993 | Kobayashi et al. | |
| 5,312,439 A | 5/1994 | Loeb | |
| 5,324,316 A | 6/1994 | Schulman et al. | |
| 5,350,413 A | 9/1994 | Miller | |
| 5,358,514 A | 10/1994 | Schulman et al. | |
| 5,411,537 A | 5/1995 | Munshi et al. | |
| 5,527,348 A | 6/1996 | Winkler et al. | |
| 5,621,369 A | 4/1997 | Gardner et al. | |
| 5,630,836 A | 5/1997 | Prem et al. | |
| 5,702,430 A | 12/1997 | Larson, Jr. et al. | |
| 5,740,257 A | 4/1998 | Marcus | |
| 5,951,459 A | 9/1999 | Blackwell | |
| 5,959,522 A | 9/1999 | Andrews | |
| 6,032,076 A * | 2/2000 | Melvin et al. | 607/61 |
| 6,048,601 A | 4/2000 | Yahagi et al. | |
| 6,240,318 B1 * | 5/2001 | Phillips | 607/61 |
| 6,324,431 B1 * | 11/2001 | Zarinetchi et al. | 607/61 |
| 6,348,070 B1 | 2/2002 | Teissl et al. | |
| 6,389,318 B1 | 5/2002 | Zarinetchi et al. | |
| 6,478,820 B1 * | 11/2002 | Weiss | 623/3.27 |
| 2002/0128690 A1 * | 9/2002 | Zarinetchi et al. | 607/33 |

FOREIGN PATENT DOCUMENTS

| | | |
|---|---|---|
| JP | 7046164 | 2/1995 |
| WO | 200002212 | 1/2000 |

OTHER PUBLICATIONS

Altieri, Frank et al., "Progress Towards a Totally Implantable Artificial Heart," Cardiovascular Science and Technology: Basic and Applied, 1 Precised Proceedings, pp. 213-216 (1989-1990).

Bearnson, G.B. et al., "Electronics Development for the Utah Electrohydraulic Total Artificial Heart," Sixth Annual IEEE Symposium on Computer-Based Medical Systems, pp. 247-252 (1993).

Callawaert, L. et al., "A Programmable Impantable Stimulator with Percutaneous Optical Control," Ninth Annual Conference of the Engineering in Medicine and Biology Society (1987).

Fraim, Freeman W., et al., "Performance of a Tune Ferrite Core Transcutaneous Transformer," IEEE Transactions on Bio-medical Engineering, vol. 18, No. 5 (1970).

Galbraith, Douglas C. et al., "A Wide-band Efficient Inductive Transdermal Power and Data Link with Coupling Insensitive Grain", IEEE Transactions on Biomedical Engineering, vol. 34, No. 4 (1987).

Mitamura, Yoshinori et al., "A Transcutaneous Optical Information Transmission System for Implantable Motor-drive Artificial Hearts," ASAIO Transactions, vol. 36, No. 3, pp. M278-M280 (1990).

Mitamura, Yoshinori et al., "Development of an Implantable Motor-Driven Assist Pump System," IEEE Transactions on Biomedical Engineering, vol. 32, No. 2, pp. 146-156 (1990).

Mitamura, Yoshinori et al., "Development of Motor Driven Assist Pump Systems," IEEE/Ninth Annual Conference of the Engineering in Medicine and biology Society (1987).

Mohammed, Osama A. et al., "A Miniature DC-DC Converter for Energy Producing Implantable Devices," IEEE/Ninth Annual Conference of the Engineering in Medicine and Biology Society, pp. 1147-1148 (1987).

Mohammed, Osama A. et al., "Design of Radio Frequency Powered Coils for Implantable Stimulators," IEEE/Ninth Annual Conference of the Engineering in Medicine and Biology Society, pp. 1378-1379 (1987).

Phillips, Richard, "A High Capacity Transcutaneous Transmission System," High Capacity Transcutaneous Energy Transmission System, pp. M259-M262 (1995).

Product Description from Raychem of HeatPath GTQ 1540.

Rintoul, Thomas C. et al., "Continuing Development of the Cleveland Clinic-Nimbus Total Artificial Hearth," ASAIO Journal, pp. M168-M171 (1993).

Sherman, C. et al., "Transcutaneous Energy Transmission (tet) System for Energy Intensive Prosthetic Devices," Progress in Artificial Organs, pp. 400-404 (1986).

Sutton, George W. "A Miniaturized Device for Electrical Energy Transmission Through Intact Skin-Concepts and Results in Initial Tests," Artificial Organs, vol. 5., Abstracts (1981).

Weiss, W.J. et al., "A Telemetry System for the Implanted Total Artificial Heart and Ventricular Assist Device," IEEE/Ninth Annual Conference of the Engineering in Medicine and Biology Society, pp. 186-187 (1987).

Weis, William J. et al., "Permanent Circulatory Support Systems at the Pennsylvania State University," IEEE Transactions on Biomedical Engineering, vol. 37, No. 2, pp. 138-145 (1990).

Geselowitz, David B. et al., "The Effects of Metals on a Transcutaneous Energy Transmission System," IEEE Transactions on Biomedical Engineering, vol. 39, No. 9, pp. 928-934 (1992).

Miller, John A. et al., "Development of Transcutaneous Energy Transmission System," ASAIO Journal, vol. 39, No. 3, pp. M706-M710 (1993).

Mitamura, Yoshinori et al., "Development Transcutaneous Energy Transmission System," Artificial Heart 2/Proceedings of the 2nd International Symposium on Artificial Heart and Assist Device, (TA. Akutsu & H. Koyanagi, eds.), Tokyo: Springer-Verlag, pp. 344-347 (1998).

Mussivand, Tofy et al., "Transcutaneous Energy Transfer System Performance Evaluation," Artificial Organs, vol. 17, No. 11, pp. 940-947 (1993).

Mussivand, Tofy et al., "Remote Energy Transmission for Powering Artificial Hearts and Assist Devices," Artificial Heart 6/6th International Symposium on Artificial Heart and Assist Devices, (T. Akutsu & H. Koyanagi, eds.). Tokyo: Springer-Verlag, pp. 344-347 (1998).

Myers, George H. et al., "A Transcutaneous Power Transformer", Transactions American Society for Artificial Internal Organs, vol. 14, pp. 210-214 (1968).

Sherman, C. et al., "Energy Transmission Across Intact Skin for Powering Artificial Internal Organs," Trans Am. Soc. Artif. Intern. Organs, vol. 27, pp. 137-141 (1981).

Weiss, William J. et al., "A Completely Implanted Left Ventricular Assist Device," ASAIO Journal pp. M427-M432 (1993).

Daily transcript for Jan. 24, 2000.
Daily transcript for Jan. 26, 2000.
Daily transcript for Jan. 27, 2000.
Daily transcript for Jan. 28, 2000.
Daily transcript for Jan. 31, 2000.
Daily transcript for Feb. 1, 2000.
Daily transcript for Feb. 3, 2000.
Deposition transcript of Robert T.V. Kung on Apr. 8, 1999.
Deposition transcript of Robert T.V. Kung on Apr. 9, 1999.
Deposition transcript of Farhad Zarinetchi on Apr. 7, 1999.
Deposition transcript of Farhad Zarinetchi on Aug. 25, 1999.
Deposition transcript of Burt Ochs on Apr. 28, 1999.
Deposition transcript of Robert T.V. Kung on Aug. 26, 1999.
Deposition transcript of Farhad Zarinetchi on Jan. 7, 2000.
Deposition transcript of Burt D. Ochs on Jan. 7, 2000.
Deposition transcript of Craig Sherman on Jan. 7, 2000.
Deposition transcript of Mark N. Horenstein on Jan. 17, 2000.

* cited by examiner

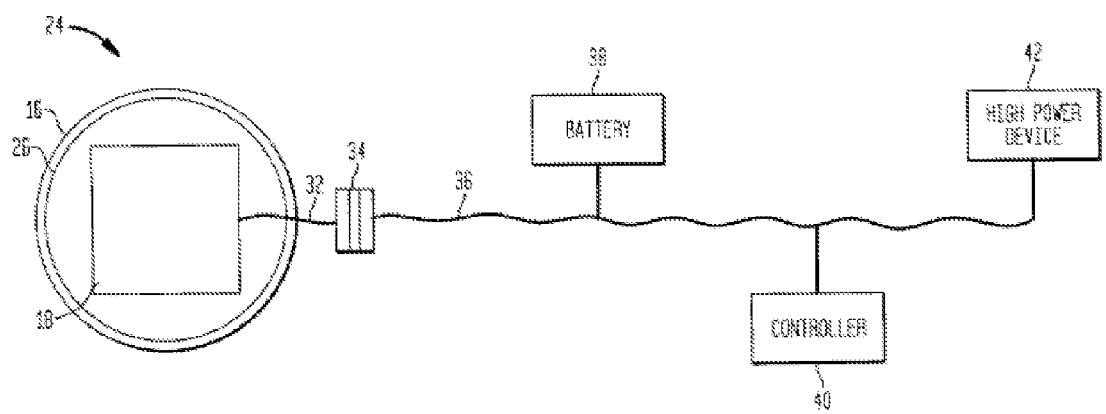

IMPLANTED TET OBJECT/INTERFACE MAP

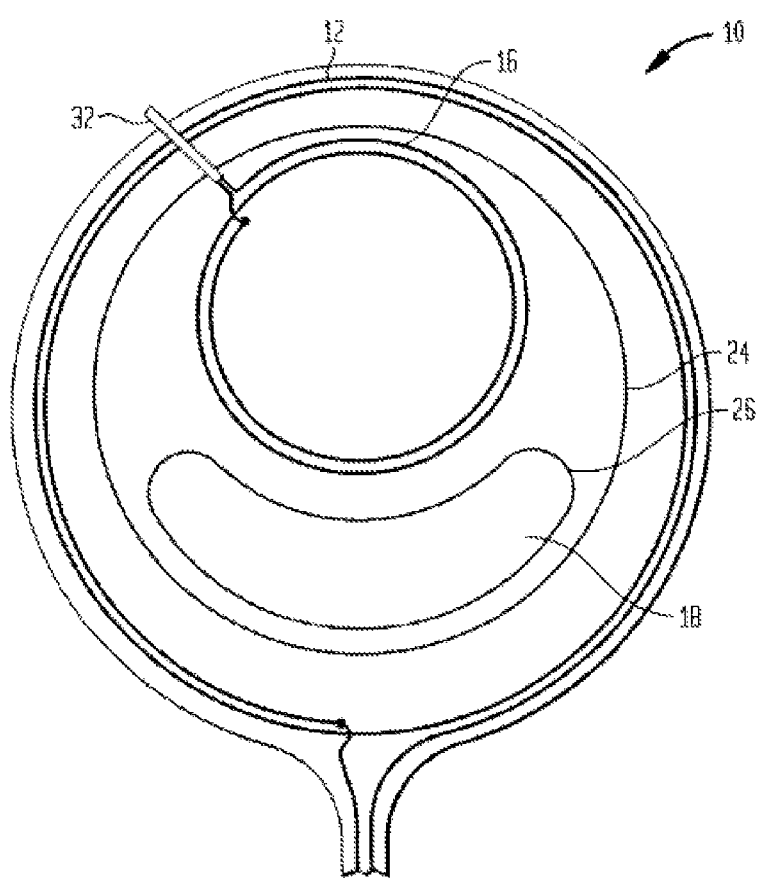

ary coil.

TRANSCUTANEOUS ENERGY TRANSFER MODULE WITH INTEGRATED CONVERSION CIRCUITRY

RELATED APPLICATIONS

This application is a divisional of U.S. patent application Ser. No. 10/316,138, filed Dec. 10, 2002, and now U.S. Pat. No. 8,489,200, entitled "Transcutaneous Energy Transfer Module with Integrated Conversion Circuitry," naming as inventors Farhad Zarinetchi and Anthony Bailey, which application is a continuation-in-part of U.S. patent application Ser. No. 09/957,330, filed Sep. 20, 2001, and now U.S. Pat. No. 6,496,733, entitled "Transcutaneous Energy Transfer Device with Magnetic Field Protected Components in Secondary Coil," naming as inventors Farhad Zarinetchi, Robert M. Hart, Michael C. Verga, and Stephen J. Keville; which application is a divisional of U.S. patent application Ser. No. 09/346,833, filed Jul. 2, 1999, and now U.S. Pat. No. 6,324,431; which application is a continuation-in-part of U.S. patent application Ser. No. 09/110,607 filed Jul. 6, 1998 entitled "TET Device with Magnetic Field Protected Components in Secondary Coil," and naming as inventors Farhad Zarinetchi and Robert M. Hart, now abandoned.

FIELD OF THE INVENTION

This invention relates to transcutaneous energy transfer (TET) devices and, more particularly, to such a device which includes power conditioning circuitry within a secondary coil.

BACKGROUND OF THE INVENTION

Many medical devices are now designed to be implantable including pacemakers, defibrillators, circulatory assist devices, cardiac replacement devices such as artificial hearts, cochlear implants, neuromuscular simulators, biosensors, and the like. Since almost all of the active devices (i.e., those that perform work) and many of the passive devices (i.e., those that do not perform work) require a source of power, inductively coupled transcutaneous energy transfer (TET) and information transmission systems for such devices are coming into increasing use. These systems consist of an external primary coil and an implanted secondary coil separated by an intervening layer of tissue.

One problem encountered in such TET systems is that the best place to locate control circuitry for converting, conditioning, amplifying or otherwise processing the signal received at the secondary coil before sending the signal on to the utilization equipment is within the secondary coil itself. However, there is also a significant magnetic field in the secondary coil resulting from the current induced therein, which field can induce heating of the components, particularly metallic components. At a minimum, such heating can influence the performance of various components, and in particular interfere with the desired uniform power applied to the equipment. In a worst case, the heating can be severe enough to cause damage or destruction to the components, which can only be repaired or replaced through an invasive surgical procedure. Such heating can also cause injury or discomfort to the patient in which the components have been implanted.

Heretofore, in order to avoid such heating, it has either been necessary to be sure that the signal induced in the secondary coil is not sufficient to generate a time-varying magnetic field which would cause potentially damaging heating of the components or to mount the components at a less convenient location. The former is undesirable because it is generally not possible to eliminate significant heating of the components while still operating the device at required energy levels, and the later solution is not desirable since the output signal from the secondary coil can reach 500 volts and above at an operating frequency that can be in excess of 100 kHz. It is preferable that such high voltage signal not pass extensively through the body and it is difficult to provide good hermetically sealed connectors for signals at these voltages. In addition, such high frequency signals can cause electrical interference with other electrical systems that may be implanted—such as, for example, an implanted controller for controlling a blood pumping device that is being powered by the TET system. It is therefore preferable that an auxiliary signal processing module, which may reduce the voltage to a value in the approximately 20 volt range, be included as close to the secondary coil as possible, a position inside the secondary coil being ideal for this purpose.

A need therefore exists for an improved technique for use with TET devices so as to enable at least selected electronic components to be mounted within the secondary coil with minimal heating of such devices. A need further exists for TET devices coupled to low voltage, high power buses for distributing power to distributed implanted devices and high power implanted devices such as blood pumping devices.

SUMMARY OF THE INVENTION

In accordance with the above, one aspect of the invention provides an implantable transcutaneous energy transfer device secondary coil module for receiving and conditioning power from a time-varying magnetic field provided by a transcutaneous energy transfer primary coil. The secondary coil module of the invention includes an inner housing, a secondary coil, power conditioning circuitry, and a low voltage, high power output means. The transcutaneous energy transfer secondary coil is disposed outside the inner housing and is configured to receive a time-varying magnetic field provided by a transcutaneous energy transfer primary coil, and to convert the time-varying magnetic field into a high voltage, alternating current electric signal within the coil. The power conditioning circuitry is mounted within the inner housing and is electrically coupled to the secondary coil. The power conditioning circuitry includes electronics for converting the high voltage, alternating current electric signal from the secondary coil into a high power, low voltage direct current electric signal. The low voltage, high power output means is electrically coupled to the power conditioning circuitry and extends outside the module for connecting the secondary coil module to a power bus for delivering power to implanted devices.

In a further aspect of the invention, an implantable blood pump energy supply system is provided having a transcutaneous energy transfer device secondary coil module, an implantable power bus electrically coupled to the secondary coil module, and a blood pumping device electrically coupled to and receiving power from the power bus. The secondary coil module has a inner housing, a secondary coil disposed outside the inner housing, power conditioning circuitry mounted within the inner housing and electrically coupled to the secondary coil, and a direct current connector electrically coupled to the power conditioning circuitry and extending outside the module. The secondary coil is configured to receive a time-varying magnetic field provided by a transcutaneous energy transfer primary coil and convert the time-varying magnetic field into an alternating current electric signal within the coil. The power conditioning circuitry includes electronics for converting an alternating current electric signal from the secondary coil into a direct current electronic signal.

In a still further aspect of the invention, an implantable transcutaneous energy transfer device secondary coil module having a low voltage output is provided for receiving a time-varying magnetic field from a transcutaneous energy transfer primary coil and converting the time-varying magnetic field to a low voltage output. The module includes an inner housing, a secondary coil, power conditioning circuitry, and a low voltage, high power output means. The transcutaneous energy transfer secondary coil is disposed outside the inner housing and is configured to receive a time-varying magnetic field provided by a transcutaneous energy transfer primary coil and to convert the time-varying magnetic field into a high voltage, alternating current electric signal within the coil. The power conditioning circuitry is mounted within the inner housing and is electrically coupled to the secondary coil. The power conditioning circuitry includes electronics for converting an alternating current electric signal from the secondary coil having a high voltage greater than or equal to about 200 volts into a direct current electric signal having a low voltage of less than or equal to about 50 volts and a high power level of greater than or equal to about 15 watts. The low voltage, high power output means is electrically coupled to the power conditioning circuitry and extends outside the inner housing for connecting the secondary coil module to a power bus for delivering power to implanted devices.

In another aspect, the invention provides a transcutaneous energy transfer system having a primary coil and a secondary coil module. The primary coil is adapted to be placed outside a patient for providing a time-varying magnetic field that passes into the patient. The secondary coil module is adapted to be implanted within the time-varying magnetic field within the patient provided by the primary coil. The secondary coil module has an inner housing including an inductive heat reducing means; a transcutaneous energy transfer secondary coil disposed outside the housing and configured to receive the time-varying magnetic field provided by the transcutaneous energy transfer primary coil and convert the time-varying magnetic field into a high voltage, alternating current electric signal within the coil; and power conditioning circuitry mounted within the housing and electrically coupled to the secondary coil, the power conditioning circuitry including electronics for converting a high voltage, alternating current electric signal from the secondary coil into a high power, low voltage direct current electric signal. An output line is electrically coupled to the power conditioning circuitry and extends outside the module to transmit the high power, low voltage direct current electric signal outside of the module.

In specific embodiments of the various aspects of the invention, the secondary coil module inner housing includes an inductive heat reducing means. In further specific embodiments, the inductive heat reducing means can include a cage formed of magnetically permeable material and the magnetically permeable material can have a magnetic permeability of between about 2000 and 5000. The cage can also include walls having a thickness adapted to maintain magnetic flux within the magnetically permeable material below saturation. The inductive heat reducing means can also be configured to maintain a total inductive heat dissipation from the power conditioning circuitry below about 150 milliwatts, even where the high voltage, alternating current electric signal in the secondary coil has a voltage of greater than or equal to about 500 volts and a frequency greater than or equal to about 200 kHz. Still further, the inductive heat reducing means can include a counterwound coil.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

FIG. 1A is a schematic diagram of a TET system and power bus of the invention;

FIG. 1C is a diagram of a TET system according to the invention in which a housing containing power conditioning electronics is adjacent or proximate to a secondary coil within a secondary coil module wherein the housing and secondary coil are both within a time-varying electromagnetic field created by a primary coil;

DETAILED DESCRIPTION OF THE INVENTION

Figure 1:
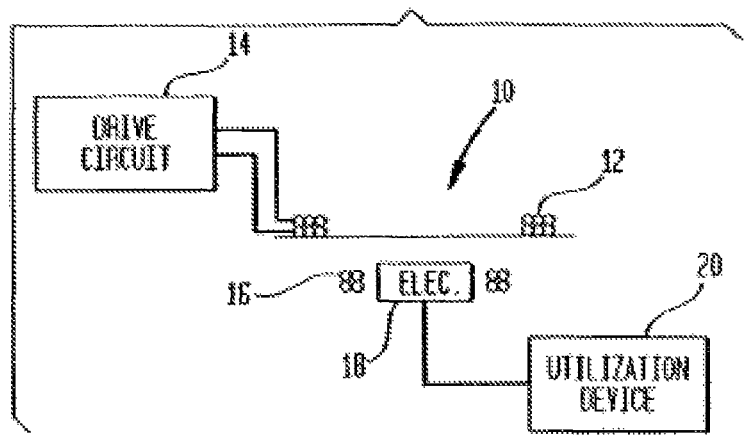
FIG. 1 is a schematic semi-block diagram of an exemplary TET system.

Referring to FIG. 1, an exemplary TET system 10 is shown which includes a primary coil 12 connected to receive an alternating drive signal from an appropriate drive circuit 14 and a transcutaneously mounted secondary coil 16 having signal processing electronics 18 mounted therein. The signal from electronics 18 is applied to operate a utilization device 20 which may for example be a blood pump, artificial heart, defibrillator, or other implanted device requiring power or other signals applied thereto.

For a number of reasons, it is desirable for electronics 18 to include power conditioning circuitry—such as, for example, rectifying or converting circuitry, regulating circuitry, monitoring circuitry, or other circuitry known for use in modifying power signals, within a secondary coil module. In the exemplary system diagram of FIG. 1A, a secondary coil module 24 is illustrated as including an inner housing 26 with the secondary coil 16 provided outside the inner housing. Secondary electronics 18 are provided inside inner housing 26 and are electronically coupled to low voltage line 32 and low voltage connector 34. Secondary coil module 24 can be encased in an outer housing to provide a sealed housing for implantation within a patient (see, e.g., outer housing 702 below), for example by overmolding the module with an epoxy and may further be coated with a biocompatible agent or have a velour material attached. Connector 34 preferably extends outside secondary coil module 24, meaning that connector 34 can extend outside of inner housing 26, and, if present, an outer housing of the module 24.

A high power, low voltage bus 36 can be connected to low voltage connector 34 to bus power to other portions of an implanted system such as battery 38 (which may use power to charge the battery or provide power when operating in battery power mode, or some combination thereof), controller 40, and a high power medical device such as a blood pumping device or a total artificial heart. A person of ordinary skill in the art will recognize that more or fewer components may be connected to low voltage bus 36, for example, power could be provided to high power medical device 42 through controller 40, or battery 38 and controller 40 could be integrated into the same module.

Figure 1B:
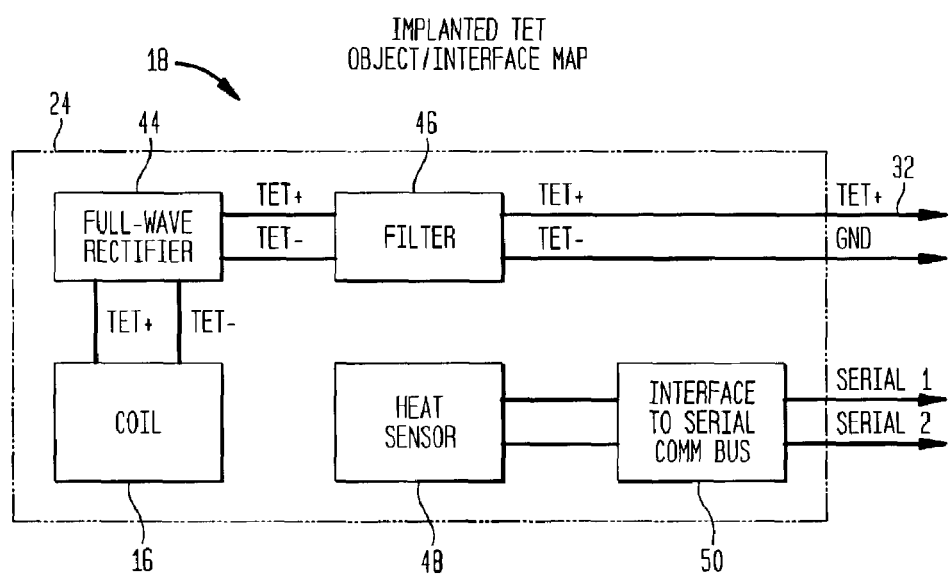
FIG. 1B is an interface map showing the electronics from the TET system of FIG. 1A.

For providing power for use by a high power implanted medical device 42, approximately 15 to 50 watts of power will typically be supplied on bus 36, or more specifically, about 20 watts. In order to supply this level of power to high power implanted medical device 42, high voltages (500 to 1000 volts) and high frequencies (200 kHz or higher) are produced in secondary coil 16. FIG. 1B provides an exemplary interface map for secondary coil module 24 to further illustrate the secondary electronics 18 contained therein. This figure shows a secondary coil 16 electrically coupled to secondary electronics 18, which in this case includes a full wave rectifier 44 and a filter 46, and leading to low voltage output 32. In the illustrated embodiment, secondary electronics 18 also includes a heat sensor 48 and an interface 50 to a communication bus for communicating sensor information to implanted controller 40. The output provided on low voltage output 32 is generally less than or equal to about 50 volts at the desired power levels, or more specifically, about 30+/−2 volts at a constant output of about 35 watts, or between about 24 and 45 volts for a pulsating load between about 0 and 45 watts.

In one exemplary embodiment, secondary coil 16 consists of 12 turns of Litz wire in a three-inch diameter coil. Secondary coil 16 can also be connected to a series-resonant tank circuit and a rectifier circuit that converts the RF power output of the tank circuit to DC power. The rectifier circuit may utilize Schottky diodes in a bridge configuration or use another rectifying circuit known in the art. An autoregulation circuit, such as a buck type DC/DC converter that regulates the output of the rectifier to a desired DC voltage may also be included. Of course, a person of ordinary skill in the art will be aware of other or different circuits that could achieve the desired output.

A system of the invention having conversion electronics incorporated within secondary coil module 24 to provide a single integrated secondary module having a low voltage, high power output solves a number of problems in the art. Placing the conversion electronics within the secondary coil module instead of other modules reduces the amount of electrical noise (note the frequencies and voltages produced in the secondary coil as described above) that might interfere with more sensitive electronic components such as controller 40.

Placing the conversion electronics within the secondary coil module as opposed to within other modules in a distributed implanted medical system also increases the reliability of the various modules as the conversion electronics dissipate a large amount of heat, raising the ambient temperature (and thus lowering the reliability) of the other electronics that share a module with it. In addition, providing conversion at the secondary coil module allows all connectors in the system to be smaller low voltage connectors, and further eliminates any need for high voltages to be transmitted on implanted cables through the body. Still further, placing the conversion electronics within the secondary coil module means that the conversion electronics do not have to be packaged in a separate module, which would further have to be implanted within the patient. While the illustrative embodiment shows electronics 18 surrounded by secondary coil 28, the advantages of the invention also apply where electronics 18 are proximate or adjacent to secondary coil 28, in particular, where both the secondary coil and the electronics are provided within the time-varying magnetic field provided by primary TET coil 12 as is illustrated in FIG. 1C (while the embodiment in FIG. 1C illustrates a side-by-side proximity, a person of ordinary skill in the art will recognize that other configurations, including vertical displacement between the secondary coil and the housing/electronics). In such an embodiment, high voltage, high frequency signals are not transmitted through the body, and inner housing 26 protects electronics 18 from inductive heating from time-varying magnetic field, thus providing the advantages of the invention without the disadvantages of prior art approaches.

A further advantage of the system of FIG. 1A is that the low voltage connector 34 and low voltage power bus 36 provide the system with greater reliability and with greater ability to repair modules without disturbing other modules or their power requirements. For example, if the power electronics 18 or secondary coil 28 itself were to fail, secondary coil module 24 could readily be swapped out, or the bus 36 powered by providing a DC power source to connector 34 so that power can be maintained or supplemented even where secondary coil module 24 must be removed for a period of time.

Despite these many advantages, no implanted TET system for transmitting high power to devices such as ventricular assist or artificial heart (i.e., blood pumps) has successfully included conversion electronics within a secondary coil module as described by the present inventors. This is true primarily because for high power applications (not including low power applications such as pace makers, cochlear implants, or trickle charging, each of which typically operate using only milliwatts (less than a watt, and typically less than a tenth of a watt, of power) the alternating magnetic field that transmits power to the secondary coil causes severe inductive heating within any electronics placed within the coil, leading to patient tissue damage and/or failure of the electronics. (See, e.g., Weiss et al., "A Completely Implanted Left Ventricular Assist Device, Chronic In Vivo Testing," ASAIO Journal, Vol. 39(3), pp. M427-M432 (July-September 1993) where power conditioning electronics were move from the secondary module to prevent tissue damage).

Figure 3A:
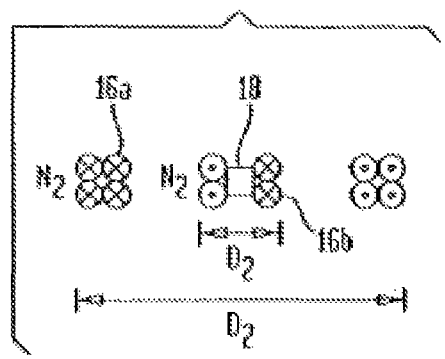
FIGS. 3A and 3B are a side-sectional view and a top plane view respectively of a secondary coil and electronics in accordance with another embodiment of the invention.
Figure 3B:
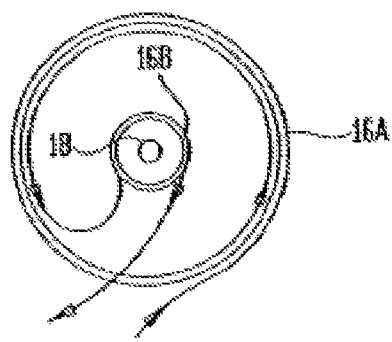
Figure 3C:
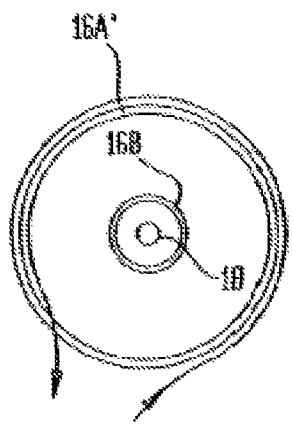
FIG. 3C is a top view for an alternative of the embodiment illustrated in FIGS. 3A and 3B.
Figure 4A:
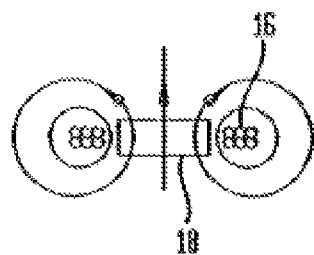
FIGS. 4A, 4B and 4C are side-sectional views of the secondary coil and electronics illustrating the magnetic field lines at the secondary for the embodiment shown in FIG. 1, FIG. 2, and FIGS. 3A-3C respectively.

As illustrated in FIG. 4A, the magnetic field lines generated by the secondary coil 16 pass through the electronics 18, resulting in heating of the electronics and, in particular, metal portions thereof. This can cause undesired variations in the outputs from this device or, worst case, in component failure. In accordance with certain aspects of the present invention, FIGS. 2 and 3A-3C illustrate two techniques for reducing inductive heating of such electronic components 18 by the magnetic field generated by the primary and secondary coils.

Figure 2:
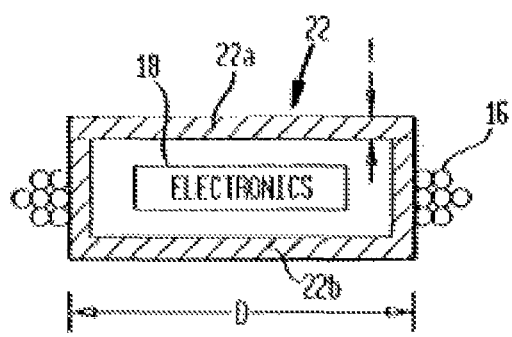
FIG. 2 is a cutaway sectional view of the secondary coil and electronics for a system of the type shown in FIGS. 1 and 1A in accordance with an embodiment of the invention.

Referring to FIG. 2, the electronics 18 are fully enclosed within an inner housing 26 comprising a cage 22 formed of a high magnetic permeability material, the material for cage 22 preferably having a magnetic permeability in the range of approximately 2000-5000. Cage 22 is formed of a base 22A and a lid 22B which are fitted and held together in a manner known in the art which minimizes interruption of magnetic field lines passing through the cage. For a preferred embodiment, the material utilized for the cage is MnZn ferrite (Phillips 3F3), although other high magnetic permeability materials now or later developed may be used. The material is preferably one formulated for high frequency application with low power loss. Since it is desirable that cage 22 be as light (have minimal mass) as possible, the wall thickness (t) of the cage should be no thicker than is required to protect electronics 18 therein, preferably while minimizing heat loss. In particular, the thickness should be the minimum thickness for the material that provides magnetic field values in the material which are well below saturation, saturation preventing the flux from being guided effectively, and below the level that would lead to significant (for example, greater than 100 mw) heat dissipation in the material under operating conditions. Saturation in the cage is a function of magnetic field strength, while heat generation is a function of both magnetic field strength and frequency. For a ferrite cage material, the field strengths and frequencies at which these effects occur can be tabulated. With a given set of operating conditions, field strength or flux density increases with decreasing wall thickness. The magnetic field strength B may be determined by measurement at the top surface of the cage 22, and the total flux $\Phi_t$ may be determined as the integral of B over the surface. This flux is guided through the sidewalls of the cage, density being highest in these sidewalls. The magnetic flux in the walls may then be calculated as the total flux divided by the cross sectional area of the wall:

$$B_{max} = \frac{\Phi_t}{(\pi D t)}$$

A thickness t may be chosen so that $B_{max}$ is below the saturation level. In an alternative embodiment, the thickness t is also chosen so that the total heat dissipation at the operating frequency is less than 100 mw. In another embodiment, the thickness t is also chosen so that the total heat dissipation at the operating frequency is between 50 and 100 mw. In a still further embodiment, the thickness t is also chosen so that the total heat dissipation at the operating frequency is less than 150 mw. In another embodiment, the thickness t is also chosen so that the total heat dissipation is between 70-90 mw. Still further, these heat dissipation goals may be achieved at operating conditions such as those described herein, for example, with secondary coil voltage greater than or equal to about 500 volts, secondary coil frequency at greater than or equal to about 200 kHz, and/or including the provision of at least 15 watts output at less than or equal to 50 volts.

Figure 4B:
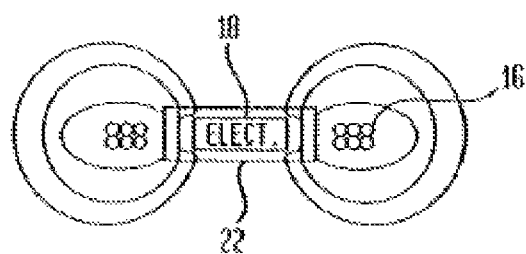

For an exemplary embodiment using the material previously indicated, wall thickness (t) is approximately 0.06 inches, and the diameter (D) of the cage for this embodiment is approximately 1.9 inches. However, these dimensions may vary significantly with application, for example the size of secondary coil 16, the electric energy applied thereto and the like. Further, the thickness of the cage need not necessarily be sufficient to divert all magnetic flux lines from the electronic 18 so long as it is effective to divert sufficient magnetic flux lines so as to prevent any significant heating of the electronic components. FIG. 4B illustrates the magnetic field for secondary coil 16 when a cage 22 of the type shown in FIG. 2 is employed. From FIG. 4B, it can be seen that the magnetic field is concentrated in the high permeability material of the cage so that the field at the electronic components 18 is reduced to nearly zero, with the magnetic field concentration being higher in the sidewalls of the cage than in the top and bottom walls. Thus, overall cage thickness and weight may in some instances be reduced by making the sidewalls thicker to accommodate the flux therein, with the top and bottom walls of the cage being thinner.

In one preferred embodiment, the optimal thickness of the cage wall has the lightest weight (lowest mass) without causing excessive heat dissipation. To have the lightest cage 22, the cage wall thickness is reduced, resulting in an increase in the magnetic flux density, B. To satisfy operation without excessive heat dissipation, B must be kept below the saturation density, $B_{max}$, for the selected cage material. Should $B_{max}$ be exceeded, the heat dissipation of the material increases dramatically. The combination of these two requirements, then, results in the desired requirement that $B_0 = B_{max}$, where $B_0$ is the flux density at the highest possible magnetic field strength for the device.

$B_0$ at any given point along the cage can be manipulated by varying the cage wall thickness. The design consideration is to reduce the cross sectional area of the cage so that $B_0$ is less than or equal $B_{max}$ along a substantial portion of the cage wall. An example of an algorithm for this process for a cylindrically symmetric cage includes first assuming a uniform thickness for the cage wall. Then, the total flux for highest power transfer within the cage walls, i.e. $\Phi_0$ using the relationship $B_0 = \Phi_0/Lt$, where L is the perimeter of the cage 22 at the point of interest and t is the cage thickness wall. Given that L is determined by other design considerations, t can be adjusted so that $B_0 = B_{max}$.

While for certain embodiments, the material of cage 22 is of a ferrite material, other high permeability materials might also be utilized such as, for example, laminated iron materials. For ease of fabrication, it may also be desirable to form the cage as three or more distinct segments, for example a top and bottom disk with a cylinder for the sidewalls, the disks and sidewalls being held together by a suitable epoxy, solder or other suitable means known in the art. This form of fabrication may be particularly desirable where the sidewalls are of a different thickness than the top and bottom walls. Preferably, the break in material continuity is minimized to avoid a significant reduction in the efficiency at which the magnetic field is conducted through the cage. Finally, forming the cage of alternate layers of ferrite material with high thermal and magnetic conductivity and epoxy or other similar material with low thermal and magnetic conductivity, results in a cage which is more anisotropic for magnetic flux flow, and thus provides potentially better flux guidance. In particular, such construction provides a lower reluctance path for the magnetic flux and magnetic fields through the ferrite layers then in a direction perpendicular thereto.

FIGS. 3A and 3B illustrate an alternative embodiment of the invention wherein reduced magnetic field at electronic components 18 is achieved by dividing the secondary coil into an outer coil 16A and an inner coil 16B which is counter-wound with the coil 16A so as to provide an opposing field. In this embodiment, the two sets of coils are connected so that the same current flows in each, and the secondary coil module inner housing in this embodiment can be any structure that serves to hold electronic components 18 within inner coil 16B. The relative diameters of the two coils, $D_1$ and $D_2$ and the number of turns for the coils, $N_1$ and $N_2$, are adjusted so that their separate contributions to the total magnetic field at the location of components 18 significantly cancel each other. In achieving this objective, the field generated in the central region by a flat outer coil 16A is given by:

$$B_1 = \frac{\mu N_1 i}{D_1}$$

while the field generated by the inner coil 16B in the central region of the coil is given by:

$$B_2 = \frac{\mu N_2 i}{D_2}$$

When the strengths of these two fields are selected to be equal, the ratio between the outer and inner windings becomes:

$$\frac{N_1}{N_2} = \frac{D_1}{D_2}$$

Using these criteria with an illustrative embodiment where $D_1$=2.5 inches, $D_2$=1.5 inches and $N_1$=19, a value for $N_2$=11.4 would be obtained. However, for this implementation, because the inner coil was slightly elongated along the field direction, a preferred value for $N_2$ was found to be 7. Therefore, while the four values (the N and D values) can be calculated to achieve the desired magnetic field cancellation for a given application, it has been found to be easier and more accurate to select the parameters empirically, for example by selecting three of the parameters to achieve substantial field cancellation and then adjusting the fourth parameter until the field at the components 18 has been reduced so that there is no significant heating of the metal components thereof. Thus, assuming the other three values are given, an $N_2$ might be determined as follows:

1. Wind the outer coil with the predetermined number of turns (19 in the example given).
2. Insert a magnetic field monitoring device such as a gauss meter in the central region of the coil.
3. Apply a dc current through the outer coil and monitor the magnetic field in the central region.
4. Locate one of the ends of the outer coil and using the wire extension from this coil, start winding the inner coil in the opposite direction of the outer coil.
5. As the inner coil is wound, monitor the strength of the magnetic field in the central region. Stop winding the inner coil when this field reaches zero.

Other empirical procedures might similarly be used for determining the parameter values in order to achieve substantial field cancellation at the center of the coil. For example, the inner coil could be wound and the system can be tested at operating conditions to determine whether the magnetic field measured would result in heat dissipation in the system that is less than or equal to 150 mw, 100 mw, or 90 mw as described above for the ferrite box embodiment.

Figure 4C:
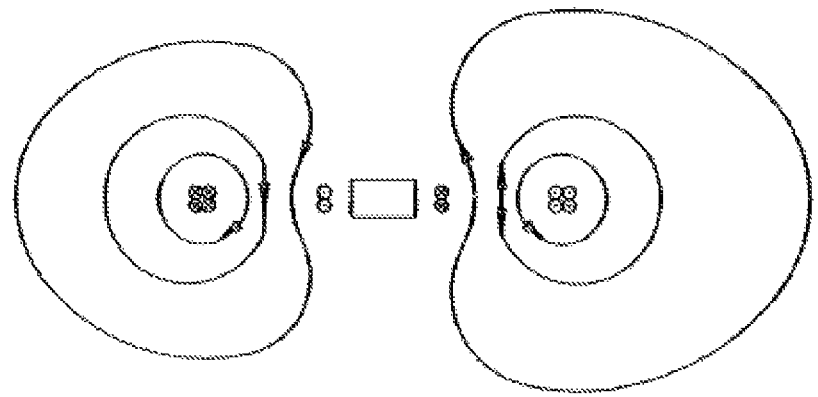

FIG. 4C illustrates a magnetic flux pattern that might be achieved with the winding pattern of FIGS. 3A-3B. From FIG. 4C, it can be seen that the magnetic field at components 18 can be reduced to substantially zero utilizing this technique. However, since this technique involves significant signal cancellation in the secondary coil, it results in reduced energy transfer efficiency for the device. It may therefore not be suitable for use in applications where high-energy transfer efficiency is required.

FIG. 3C illustrates an alternative to the embodiment shown in FIG. 3B which to some extent reduces the loss of energy transfer efficiency resulting from the counterflowing current in coil 16B. For this embodiment, coil 16B' is a few turns of wire, for example one or two, having the diameter $D_2$ but not electrically connected to the windings 16A'. The magnetic flux resulting from current flow in windings 16A' induce a current in winding 16B' which in turn produce a magnetic field countering that generated by that winding 16A. By suitable selection of both the number and diameter of the windings 16A' and 16B', field cancellation such as that shown in FIG. 4C can be achieved.

In an alternative embodiment, the cage of the present invention is configured to increase the permeability in a flux pathway between the primary and secondary coils that is closest to the secondary coil. In one embodiment this is achieved by extending the high permeability shield material of cage 22 to a location within the flux pathway. This increases the total permeability of the flux pathway with a corresponding increase in coupling between the primary and secondary coils.

Figure 5:
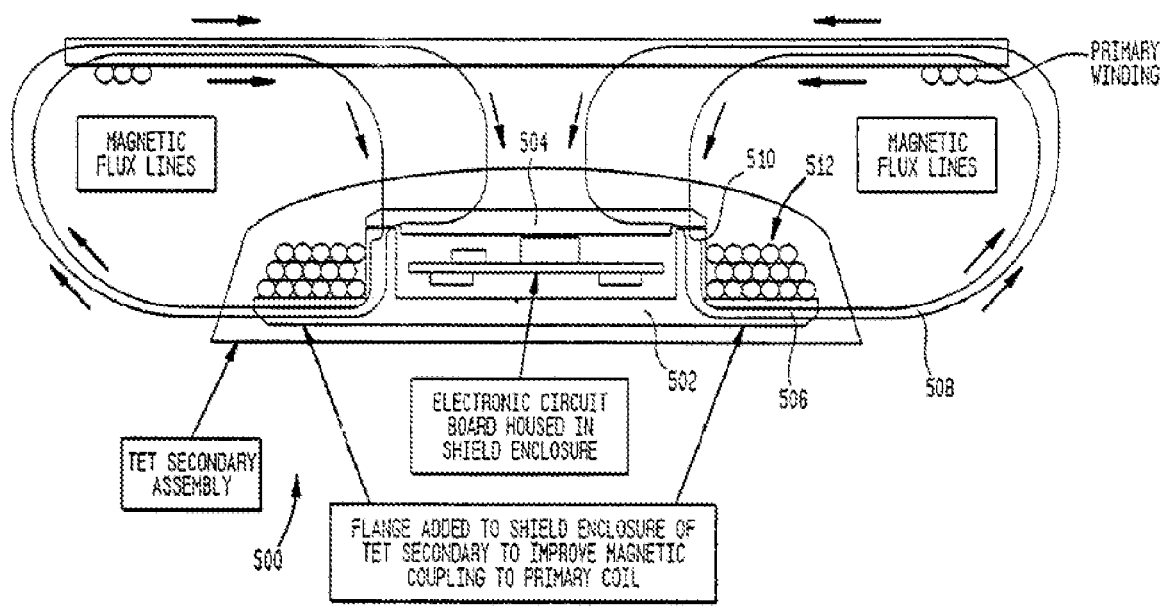
FIG. 5 is a cross-sectional view of an alternative embodiment of a cage of the present invention having flanges or extensions extending therefrom.

An exemplary implementation of this alternative embodiment of the cage is illustrated in FIG. 5. As shown therein, the inner housing comprises a cage 500 including a base 502 and a lid 504. In this illustrative embodiment, base 502 is cylindrical while lid 504 is shaped in the form of a disk. Base 502 includes and integral flange 506 that extends the cage material from base 502 into the magnetic flux pathway 508.

To increase the coupling between the primary and secondary coils, flange 506 is preferably in-line with the shortest flux pathway between the primary and secondary coils. In other words, flange 506 extends from base 502 immediately adjacent to secondary coil 512 to guide the magnetic flux lines back toward the primary coil. The extent to which the flange 506 extends away from base 502 is based on the mass and volume limitations of the device. However, flange 506 preferably does not have a thickness less than that which would cause saturation of the magnetic material, particularly at highest primary field strengths.

It should be understood that flange 506 may be the same or different high permeability material as base 502. In devices wherein flange 506 and cage 22 are of the same material, flange 506 and base 502 are preferably formed as a unitary device. However, in alternative embodiments, flange 506 may be attached to base 502 using well-known techniques.

Figure 6:
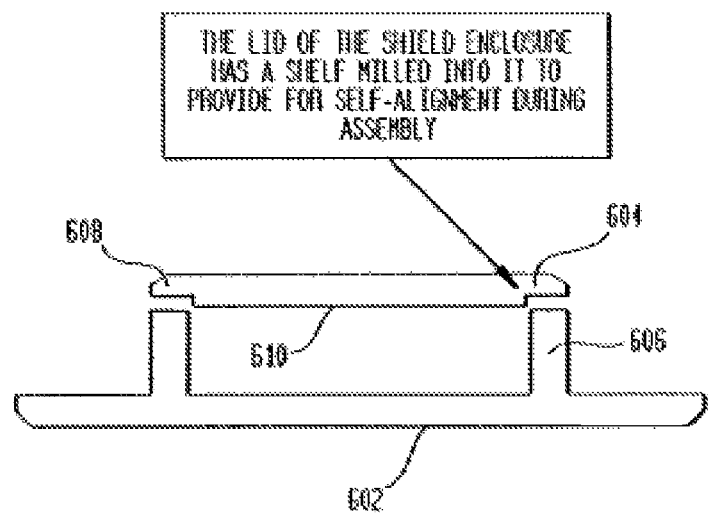
FIG. 6 is a simplified cross-sectional view of a cage in accordance with one embodiment of the present invention.

FIG. 6 is a simplified cross-sectional view of an alternative embodiment of a cage 600. Cage 600 includes a base 602 and a self-aligning or interlocking lid 604. In this illustrative embodiment, base 602 is cylindrical while lid 604 is shaped in the form of a disk. Base 602 includes vertical walls 606 onto which lid 604 is attached, typically by bonding.

Lid 604 includes an annular recessed shelf 608 circumferentially formed around mating surface 610 of lid 604. Shelf 608 is configured to receive vertical wall 606 of base 602 thereby preventing relative motion of lid 604 and base 602 during assembly. It should be understood that other features may be used to align and/or secure lid 604 with base 602, such as by threading, etc. Alternatively, mating surface 610 of lid 604 may have a track or groove configured to accept base vertical wall 606. It should also be noted that annual recessed shelf 608 may be configured as a square or any other shape to accept base 602.

Figure 7:
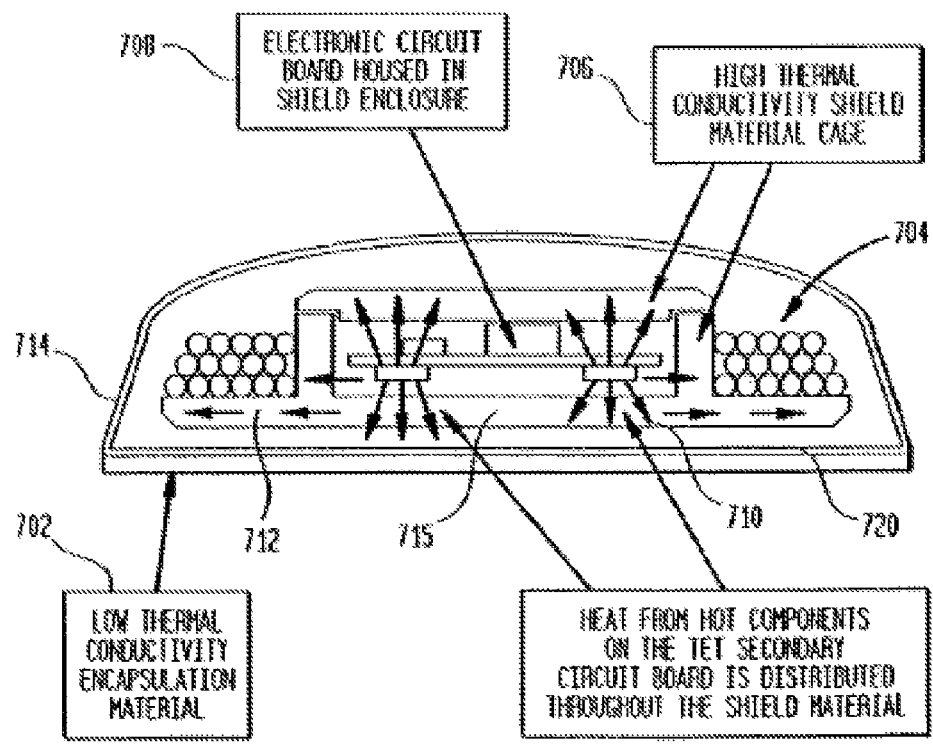
FIG. 7 is a cross-sectional view of an implantable device having a secondary coil in accordance with an alternative embodiment of the present invention.

FIG. 7 is a cross-sectional view of an implantable device outer housing 702 enclosing a secondary coil 704. Inner housing or cage 706 is positioned within secondary coil 704, as described above. Cage 706 serves to house electronic components 708 that generate heat, illustrated by arrows 710. In accordance with this embodiment of the present invention, heat in implanted device 702 is distributed to avoid localized high temperature regions as well as tissue necrosis.

Outer housing 702 is constructed of a relatively low thermal conductivity medium such as potting epoxy. Cage 706 preferably includes flange 712 similar to the flange described above with reference to FIG. 6. In accordance with this embodiment of the present invention, a heat distribution layer 714 is thermally coupled to cage 706 and outer housing 702. Heat generated by electronics 708 is transferred via conduction to cage 706. To facilitate the transfer of such heat into distribution layer 714 good thermal contact is maintained between distribution layer 714 and cage 706 using a thermally conductive medium. In addition, the largest contact area between distribution layer 714 and cage 706 suitable for the implemented design is implemented. For example, in the embodiment illustrated in FIG. 7, flange 712 provides base 715 with the greatest area over surface 720 as compared to other surfaces of cage 706. Accordingly, distribution layer 714 is thermally coupled to cage 706 at surface 720. Similarly, distribution layer 714 is preferably thermally coupled to a substantial area of outer housing 702. This provides for the substantially uniform distribution of heat along outer housing 702. In the embodiment illustrated in FIG. 7, distribution layer 714 is thermally coupled to the entire housing 702 other than the portion of outer housing 702 adjacent bottom surface 720 of cage 706.

In one embodiment, distribution layer 714 has a high thermal conductivity and a low magnetic permeability and low electrical conductivity. For example, in one preferred embodiment, distribution layer 714 is formed from alumina powder suspended in an epoxy medium. The thickness of the distribution layer 714 is preferably in the range of 2-10 mm, although other thicknesses and materials may be used for a given application. In an alternative embodiment, distribution layer 714 is comprised of multiple alternating layers of high and low heat conductivity materials.

While specific embodiments have been disclosed above for reducing the magnetic field at the center of a TET device secondary coil so as to permit device electronics to be mounted in the coil without excessive heating, it is to be understood that other techniques for achieving this objective and/or other variations on the embodiments disclosed are within the contemplation of the invention. Thus, while the invention has been particularly shown and described above with reference to preferred embodiments, the foregoing and other changes in form and detail may be made therein by one skilled in the art while still remaining within the spirit and scope of the invention, which is to be defined only by the following claims. In particular, several of the embodiments disclosed herein can be combined, For example, the ferrite box, ferrite box with flange, and counterwound coil features can be combined. By combining features and measuring the magnetic flux in at the electronics, a person of ordinary skill in the art can select from among these features to produce a system in which a desired heat dissipation maximum can be achieved at operating conditions.

What is claimed is:

1. An implantable transcutaneous energy transfer device, comprising:
   a transcutaneous energy transfer secondary coil comprising an inner winding and an outer winding, the secondary coil configured to inductively couple to a transcutaneous energy transfer primary coil, said secondary coil having an electrical signal induced therein; and
   electronic components disposed in a central region of the inner and outer windings and electrically coupled to the secondary coil, the electronic components for processing the electrical signal for powering implanted devices,
   wherein the inner winding and outer winding are configured such that a magnetic field generated by the inner winding and a magnetic field generated by the outer winding when the electrical signal is induced in the secondary coil substantially cancel one another at the central region.

2. The transcutaneous energy transfer device of claim 1, wherein the inner and outer windings are configured to maintain a total inductive heat dissipation from the electronic components below about 150 milliwatts.

3. The transcutaneous energy transfer device of claim 2, wherein inductive heat dissipation is maintained below about 150 milliwatts under operating conditions when the electrical signal has a voltage of greater than or equal to about 500 volts and a frequency greater than or equal to about 100 kHz.

4. The transcutaneous energy transfer device of claim 1, wherein the inner and outer windings are electrically connected such that the same electrical current flows in each of the inner and outer windings.

5. The transcutaneous energy transfer device of claim 4, wherein the inner winding is counterwound relative to the outer winding.

6. The transcutaneous energy transfer device of claim 1, wherein magnetic flux resulting from current flow in the outer winding induces a current in the inner winding and the current induced in the inner winding generates the magnetic field of the inner winding.

7. The transcutaneous energy transfer device of claim 1, further comprising an inner housing disposed in the central region, wherein the electrical components are contained within the inner housing.

8. The transcutaneous energy transfer device of claim 7, further comprising a heat distribution layer provided externally to the module and a thermally conductive medium providing thermal conduction between the inner housing and the heat distribution layer.

9. The transcutaneous energy transfer device of claim 7, wherein the inner winding is adjacent the inner housing and disposed between the inner housing and the outer winding.

10. The module of claim 1, wherein the electronic components are configured to process the electrical signal to reduce a voltage thereof to about 20 volts.

11. The transcutaneous energy transfer device of claim 1, further comprising an implantable medical device electrically coupled to the electronic components.

12. A transcutaneous energy transfer system, comprising:
    a transcutaneous energy transfer primary coil adapted to be placed outside a patient;
    a transcutaneous energy transfer device secondary coil module adapted to be implanted within the patient and to inductively couple to the primary coil, the secondary coil module comprising:
      a transcutaneous energy transfer secondary coil comprising an inner winding and an outer winding, the secondary coil having an electrical signal induced therein when the secondary coil is inductively coupled to the primary coil; and
      electronic components disposed in a central region of the inner and outer windings and electrically coupled to the secondary coil for processing the electrical signal,
      wherein the inner winding and outer winding are configured such that a magnetic field generated by the inner winding and a magnetic field generated by the outer winding when the electrical signal is induced in the secondary coil substantially cancel one another at the central region; and an implantable medical device electrically coupled to the electronic components for receiving power therefrom.

13. The system of claim 12, wherein the inner and outer windings are configured to maintain a total inductive heat dissipation from the electronic components below about 150 milliwatts.

14. The system of claim 12, wherein the implantable medical device is a blood pump.

15. A method for reducing inductive heating in a transcutaneous energy transfer system, comprising a transcutaneous energy transfer primary coil adapted to be placed outside a patient, a transcutaneous energy transfer secondary coil module adapted to be implanted within the patient and to inductively couple to the primary coil, the transcutaneous energy transfer secondary coil module comprising a secondary coil and electronic components disposed in a central region of the secondary coil, the method comprising:

constructing the transcutaneous energy transfer secondary coil as an inner winding and an outer winding, the secondary coil having an electrical signal induced therein when the secondary coil is inductively coupled to the primary coil; and selecting a diameter for the inner and outer windings and a number of turns for each winding such that magnetic fields in the central region substantially cancel each other.

16. The method of claim 15, further comprising implanting the secondary module in a patient.

* * * * *